(12) United States Patent
Nilsson

(10) Patent No.: US 6,555,327 B1
(45) Date of Patent: Apr. 29, 2003

(54) MONOCLONAL ANTIBODIES AGAINST S100

(75) Inventor: Olle Nilsson, Gothenburg (SE)

(73) Assignee: CanAg Diagnostics AB, Gothenburg (SE)

(*) Notice: Subject to any disclaimer, the term of this patent is extended or adjusted under 35 U.S.C. 154(b) by 0 days.

(21) Appl. No.: 09/763,897

(22) PCT Filed: Aug. 27, 1999

(86) PCT No.: PCT/SE99/01474

§ 371 (c)(1),
(2), (4) Date: Jul. 5, 2001

(87) PCT Pub. No.: WO00/12559

PCT Pub. Date: Mar. 9, 2000

(30) Foreign Application Priority Data

Aug. 28, 1998 (SE) .............................................. 9802896

(51) Int. Cl.[7] .............................................. G01N 33/53
(52) U.S. Cl. ...................... 435/7.92; 435/7.1; 435/7.94; 435/7.95; 435/975; 436/514; 436/518; 436/547; 436/548; 530/388.1
(58) Field of Search ................................. 435/7.1, 7.94, 435/975, 7.92; 436/514, 518, 547, 548; 530/388.1

(56) References Cited

PUBLICATIONS

Yang et al., Brain Res. 1995. 696(1,2):49–61.*
Kamegai et al., Acta Histochem. Cytochem. 1990. 23(2):209–218.*
Vanstapel et al., Am. J. Clin. Pathol. 1986. 85(2):160–168.*
Van Eldik, L. et al., "Production and characterization of monoclonal antibodies with specificity for the S100β polypeptide of brain S100 fractions," Proc. Natl., Acad. Sci. USA, vol. 81, pp. 6034–6038, Oct. 1984. Cell Biology.
Lindholm, L. et al., "Monoclonal Antibodies against Gastrointestinal Tumour–Associated Antigens Isolated as Monosialogangsliosides," Int. Archs Allergy, Appln. Immun., 71: 178–181 (1983).
Michetti, F. et al., "The S–100 Antigen in Cerebrospinal Fluid as a Possible Index of Cell Injury in the Nervous System," Journal of Neuerological Sciences, 1980, 44: 259–263.
Isobe, T. et al., "The Amino–Acid Sequence of the α Subunit in Bovine Brain S–100a Protein," Eur. J. Biochem. 116, 79–86 (1981), FEBS 1981.
Langlois, N. "Changes of diffuse neurofibrillary tangles with calcification (DNTC) in a woman without evidence of dementia," Letters to the Editor, p. 103.
Persson, L. et al., "S–100 Protein and Neuron–Specific Enolase in Cerebrospinal Fluid and Serum: Markers of Cell Damage in Human Central Nervous System," Stroke, vol. 18,k No. 5, Sep.–Oct. 1987.
Westaby, S. et al, "Serum S100 Protein: A Potential Marker for Cerebral Events During Cardiopulmonary Bypass," Ann. Thorac Surg. 1996; 61:88–92.
Zimmer, D. et al, "The S100 Protein Family: History, Function and Expression," Brain Research Bulletin, vol. 37, No. 4, pp. 417–429, 1995.
Kato, K. et al., "S100a•(αα) protein is mainly located in the heart and striated muscles," Biochimica et Biophysica Acta 842(1985) 146–150.
Moore, B., "Chemistry and Biology of the S–100 Protein," Scand. J. Immunol., vol. 15, Suppl. . 9, 53–74, 1982.
Isobe, T. et al., S100a$_0$(αα) Protein is Present in Neurons of the Central and Peripheral Nervous System, Journal of Neurochemistry, vol. 43, No. 5, 1984.
Nakane, P., et al., "Peroxidase–Labeled Antibody ad New Method of Conjugation," Journ. of Histochemistry and Cytochemistry, vol. 22, No. 12, pp. 1084–1091, 1974.
Moore, B. et al, "A Soluble Protein Characteristic of the Nervous System," Biochemical and Biophysical Research Communicatons, vol. 19, No. 6, 1965.
Isobe, T. et al., "The Amino–Acid Sequence of S–100 Protein (PAP I–b Protein) and Its Relation to the Calcium–Binding Proteins," Eur. J. Biochem. 89, 379–388 (1978).
Henze, G. et al., "Serum S100–A marker for Disease Monitoring in Metastic Melanoma," Dermatology, 1997, 194: 208–212.

* cited by examiner

*Primary Examiner*—Bao-Thuy L. Nguyen
(74) *Attorney, Agent, or Firm*—Browdy and Neimark, P.L.L.C.

(57) ABSTRACT

The present invention relates to novel monoclonal antibodies against the calcium binding protein S100, the use of these antibodies for the development of immunoassays for specific determination of total S100 or the different isoforms of S100 in serum, plasma, cerebrospinal fluid and other body fluids.

18 Claims, 3 Drawing Sheets

MONOCLONAL ANTIBODIES AGAINST S100

The present application is the national stage under 35 U.S.C. 371 of international application PCT/SE99/01471, filed Mar. 9, 2000, which designated the United States, and which international application was published under PCT Article 21 (2) in the English language.

FIELD OF THE INVENTION

The present invention relates to novel monoclonal antibodies against the calcium binding protein S100, the use of these antibodies for the development of immunoassays for determination of total S100 or specific determination of the different isoforms of S100 in serum, plasma, cerebrospinal fluid and other body fluids.

BACKGROUND OF THE INVENTION

S100 is a 21 kDa protein belonging to the S100/calmodulin/troponin C super family of EF-hand calcium binding proteins (for review see Zimmer et al, Brain Res Bull 37: 417–429, 1995). S100 was originally isolated by Moore and co-workers from human brain, and was originally considered as a brain specific protein (Moore, Biochem Biophys Res Commun 19: 739–744, 1965). There has today been identified ▲16 members of the S100 family based upon amino acid sequence and functional similarities (Zimmer et al. Brain Res Bull 37: 417–429, 1995).

S100 in brain tissue consists of homo- and heterodimers of $\alpha$ and $\beta$ subunits. The $\alpha$ and $\beta$ subunits show a high degree of sequence and species homology (Isobe et al, Eur J Biochem., 89: 379–388, 1978; Isobe et al. Eur J Biochem. 116: 79–86, 1981). The S100$\beta\beta$ exists in high concentration in glial cells and Schwann cells, while the S100$\alpha\beta$ is expressed in glial cells but not in Schwann cells (Isobe et al, J Neurochem 43: 1494–1496, 1984). S100$\alpha\alpha$ is present in neurones, but is mainly expressed in extra cerebral tissues such as skeletal muscle, kidney and heart (Kato and Kimura, Biochim. Biophys Acta 842:146–152, 1985). Small amounts of S100 is present in different normal human tissues: skin, chondrocytes, spleen, adipose tissue, kidney, heart, skeletal muscle and in different malignant tissues; malignant melanoma, glioma, and soft tissue tumours (Zimmer et al. Brain Res Bull 37: 417–429, 1995).

Determination of S100 in serum and CSF has shown to be useful in the management of patients with brain trauma and to evaluate neurological complications after cardiopulmonary bypass surgery (Michetti et al. J Neurol. Sci. 44: 731–743 1980; Persson et al. Stroke 18: 911–918, 1987; Ingebrightsen et al. J Neurol, Neurosurg. Psych. 59: 103–104, 1995; Westaby et al. Ann Thorac Surg 61: 88–92, 1996). Serological determination of S100 has also been shown to be useful for follow-up and in order to obtain prognostic information in patients with malignant melanoma (Henze et al. Dermatology 194: 208–212, 1997; Buer et al. Br J Cancer, 75: 1373–1376, 1997). Different disorders may be associated with changed total amount of S100$\alpha\beta$ and S100$\beta\beta$ or changed ratio between the different isoforms of S100. Therefore accurate methods for determining the total amount of S100$\alpha\beta$ and S100$\beta\beta$ as well as for determining the different isoforms of S100$\alpha\beta$ and S100$\beta\beta$ are needed.

WO 98/01471 discloses a method for determining the total amount of S100. This method comprises one step with the major drawback that information of the amount of the individual isoforms S100$\alpha\beta$ and S100$\beta\beta$ is not given, and the response for S100$\alpha\beta$ and S100$\beta\beta$ is not identical, hence the assay according to the invention gives a more accurate determination of total S100 (i.e. the sum of S100$\alpha\beta$ and S100$\beta\beta$). The method according to the present invention gives a more accurate determination of the total amount S100 since the S100$\alpha\beta$ and S100$\beta\beta$ are determined in two separate steps with specific determination of the isoforms S100$\alpha\beta$ and S100$\beta\beta$ in the individual steps. The method according to the present invention also gives accurate information of the concentration of the two isoforms S100$\alpha\beta$ and S100$\beta\beta$.

SUMMARY OF THE INVENTION

The present invention provides monoclonal antibodies against S100, and the design of immunoassays for determination of the total amount of S100$\alpha\beta$ and S100$\beta\beta$ as well as for specific determination of the different isoforms of S100, i.e. specific for either S100$\alpha\beta$ or S1000$\beta\beta$.

The invention will be useful for serological determination of total S100 and for determination of the different isoforms of S100 in the management of patients with brain damage, neurodegenerative diseases, and in the follow-up of patients with malignant melanoma, gliomas and certain soft tissue tumours.

DESCRIPTION OF THE SPECIFIC EMBODIMENTS

The present invention provides novel monoclonal antibodies against S100, and the design of immunoassays for determination of S100 in serum, plasma, cerebrospinal fluid or other body fluids.

The method comprises the establishment of monoclonal antibodies against specific epitopes of S100, the use of these antibodies for the design of immunoassays for determination of total S100, immunoassays specific for S100$\alpha\beta$ and immunoassays specific for S100$\beta\beta$.

The immunosassays are designed for, but not restricted to, immunometric (non-competitive) assay format. The antibodies according to the invention may also be used for competitive assay format. The immunoassays employ, but are not restricted to, monoclonal antibodies against specific epitopes of S100$\beta$ for catching and detection of S100. According to the invention monoclonal antibodies are preferred, but the assay according to the invention may employ polyclonal antibodies, peptides, proteins, protein or DNA fragments with essentially the same binding specificity as the monoclonal antibodies provided by the invention.

Furthermore the immunoassays employ, but are not restricted to, a solid-phase containing the S100 monoclonal antibodies for the adsorption of the S100 from the sample. The solid-phase may be wells of microtiter plates, plastic tubes, beads, magnetic particles or the like. The solid-phase may be produced from glass, polypropylene, polystyrene, and the like. The catching antibody may be bound to the solid phase by, but is not restricted to, physical adsorption, covalent binding or through biotin—avidin bridges, or the like, using methods generally known to those skilled in the art.

In the present invention a wide variety of labels are suitable for detection of the S100. Enzymes are of particular interest, including hydrolases particularly esterases and glycosidases, and oxidoreductases, particularly peroxidases. Suitable are also radioactive labels, such as 125I, 32P, 14C, 3H and the like, fluorescent compounds such as fluorescein and its derivatives, rhodamine and its derivatives, dansyl, umbelliferone, lanthanid derivatives, and the like, and chemiluminencers such as luciferin, luminol, acridinium esters and the like.

The assays according to the invention can be performed in any double epitope assay format; either two-step forward sandwich assay, one-step sandwich assay or backward sandwich assay.

In performing the assays according to the present invention, a sample (preferably 1–1000 μL) is incubated in the test receptacle containing a catching anti S100 MAb. In the preferred configuration the sample consists of serum, plasma or cerebrospinal fluid. According to the invention the sample and S100 MAb is incubated under conditions allowing binding of the S100 antigen to the catching S100 MAb. In the preferred configuration the catching antibody is immobilized to the solid-phase through biotin—streptavidin bridges. For the detection of the S100 antigen adsorbed to the solid-phase bound antibody a labeled monoclonal antibody directed against independent epitopes of S100 is added, and incubated in the test receptacle under conditions allowing the antibody to bind to the S100-antibody complex. After washing the label is detected in a system suitable for the label used.

The present invention provides antibodies specific for the different isoforms of S100 that are used as catching antibodies and antibodies, whose epitopes are not overlapping the epitopes of said catching antibodies, that are used as detecting antibodies (see Example 2.3b). Depending on the selection of catching and detecting antibodies immunoassays with the preferred specificity may be designed, i.e. assays for specific determination of S100αβ, and assays for specific determination of S100ββ.

The hybridoma cell lines S10:3, S21:4, S23:2, and S35:2, producing the monoclonal antibodies according to the invention, were deposited at the ECACC (European Collection of Cell Cultures, Centre for Applied Microbiology & Research, Salisbury, Wiltshire SP4 0JG, UK) and assigned ECACC Accession Nos. 98082619, 98082618, 98082617, and 98082616, respectively. These deposits were made on the Aug. 26, 1998. Also included in the invention are antibodies, antibody fragments or peptides with the same binding specificity as antibodies produced by the hybridoma cell lines S10:3, S35:2, S23:2, and S21:4 as shown by that they inhibit the binding of the antibody in question by >75% as measured by inhibition studies as outlined in Example 2.3b.

This invention will now be described in greater detail by reference to the following non-limiting examples and the attached figures, wherein:

FIG. 1 shows reactivity with purified S100ββ, S100αβ, and S100αα of selected S100 MAb in immunometric assays. The reactivity was determined as described in Example 2.2.

FIGS. 2A–F show the inhibition of selected S100 MAb:s as described in Example 2.3b.

EXAMPLE 1

Figure 1:
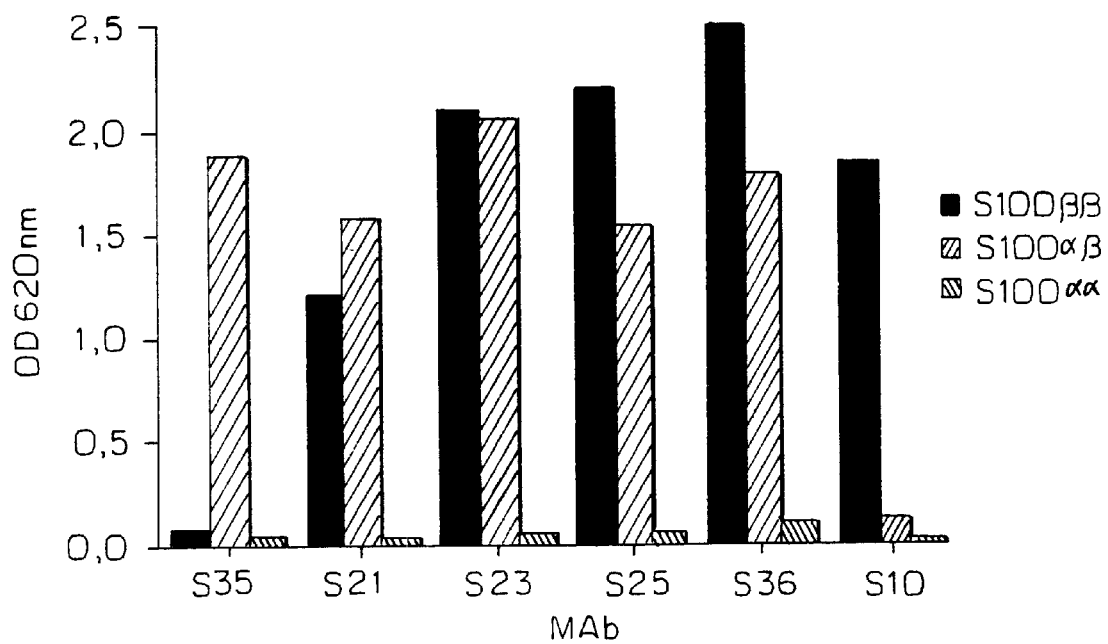
Figure 2A:
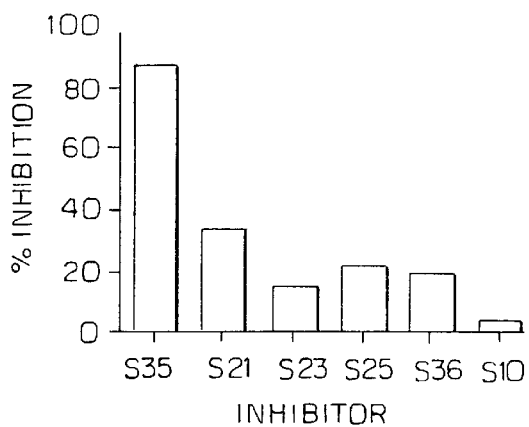
Figure 2B:
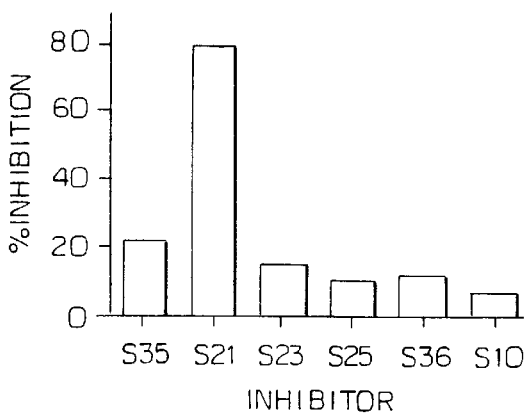
Figure 2C:
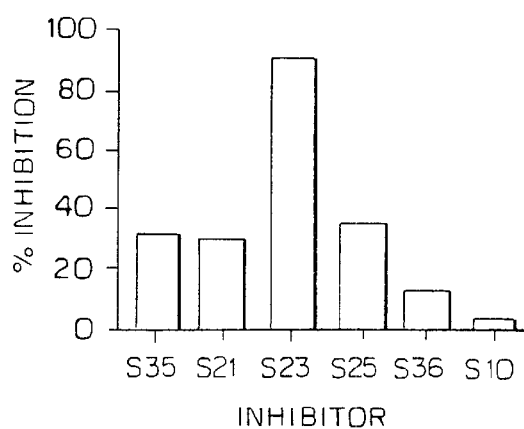
Figure 2D:
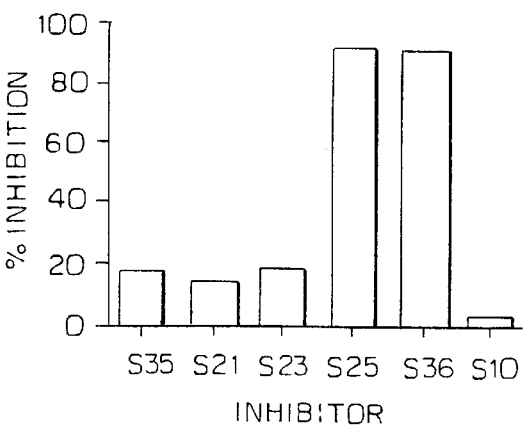
Figure 2E:
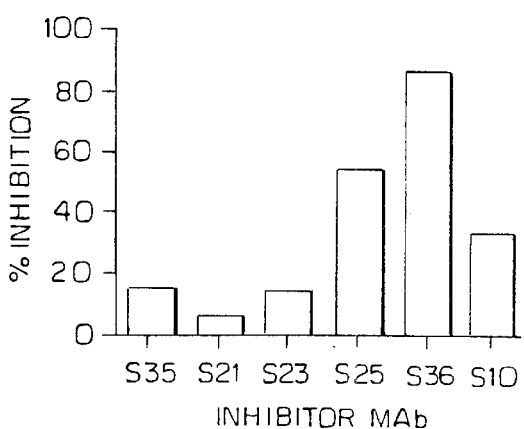
Figure 2F:
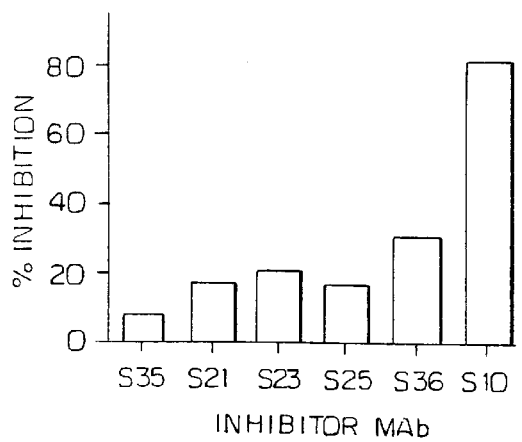

Establishment of Hybridomas and Production of Monoclonal Antibodies Specific for S100

S100ββ is commercially available from several suppliers, e.g. Affinity Research, UK; Calbiochem, US; Sigma Chemical Co, US; HyTest, Finland. The commercially available S100ββ may be used as immunogen for establishment of monoclonal antibodies. S100ββ may also be isolated from human or bovine brain following methods available in the literature (Moore, Scand J Immunol 9: 53–74, 1982).

In the preferred procedure Balb/c mice were immunised intra peritoneally with 10–50 μg of S100ββ in Ribi adjuvant. After the immunisation and 3–4 booster doses during 60–90 days, with the same antigen or mixture of S100ββ/S100αβ, spleen cells from the immunised mice were fused with P3×63Ag 8 myeloma cells as described (Lindholm et al. Int. Arch Allergy and Appl. Immunol. 71: 178–181, 1983).

Hybridomas producing antibodies reacting with S100 were selected by screening of hybridoma supernatants in microtiter wells coated with affinity purified polyclonal antiserum against mouse IgG+M, (Jackson Immuno Res Lab, US). The wells were then incubated with S100ββ antigen, and after washing the bound S100 antigen was detected by incubation with polyclonal Rabbit Anti S100 and HRP labelled Swine Anti Rabbit Ig (Dako AS, Denmark).

Clones producing antibodies reacting with S100ββ and S100αβ, but negative for S100αα were cloned twice by limiting dilution. Monoclonal antibodies were produced by in vitro cultivation of the hybridoma clones by inoculation of $10^4$ cells/mL in DMEM, 5% Fetal Calf Serum in roller bottles and allowed to grow for 10–14 days. The monoclonal antibodies were then purified from the culture medium by Protein A (Bioprocessing Ltd, Durham, UK) affinity chromatography according to the manufacturers recommendation.

The S10, S21, S23, and S35 monoclonal antibodies (MAb), produced by hybridoma cell-lines S10:3, S21:4, S23:2, and S35:2, respectively, were selected for the design of immunoassays according to the invention.

EXAMPLE 2

Characterization of the Antibodies 2. 1. Determination of Isotype

The isotype of the antibodies were determined after adsorption of the established antibodies in microtiter plats coated with antibodies against mouse IgG+A+M antibodies (Zymed Lab. Inc, CA, US). The isotype were then detected by incubation with HRP labeled antibodies specific for Mouse IgG1, Mouse IgG2a, Mouse IgG2b, Mouse IgG3, Mouse IgA and Mouse IgM antibodies (Zymed Lab. Inc., CA, US), and incubation with OPD substrate and determination of OD at 450 nm. All antibodies according to the invention were found to be of the IgG1 isotype.

2. 2 Reactiuity with S100ββ, S100αβ and S100αα

Reactivity with S100ββ, S100αβ and S100αα of the established S100 MAb:s was determined in enzyme immuno-metric assay (EIA) with the S100 MAb adsorbed to the wells of microtiter plates, incubation with purified S100 antigen, and detection of bound S100 with polyclonal Rabbit Anti S100 followed by HRP Swine Anti Rabbit Ig (Dako AS, Denmark).

S100 MAb were coated in the wells of Nunc MaxiSorp Immunoplate (Nunc AS, Denmark), by incubation of S100 MAb solution over night at room temperature (200 μL/well, 10 μg MAb/mL in 0.2 M NaH2PO4). After washing unspecific binding were blocked by incubation with 300 μL/well of 50 mM Tris, pH 7.8, 0.1 g/L BSA, 60 g/L Sorbitol.

In the EIA 50 μL of S100ββ, S100αβ, or S100αα (50 μg/L), (Affinity Res. Inc. UK), and 100 μL of Assay Buffer (50 mM Tris, 0.15 M NaCl, 10 g/L BSA, 0.5 g/L bovine Ig, 0.1 g/L methylisothiazolone, pH 7.75) were incubated in duplicates in the S100 MAb coated mnicrotiter wells. After 1 h incubation with constant shaking the wells were washed twice, and 100 μL of Rabbit Anti Human S100 (Dako AS, Denmark), diluted 1/3000 in PBS-1% BSA, 0.1% Tween 20 was added, and the incubation continued for 1 h. After additional washings bound Rabbit Anti S100 was determined by incubation with HRP Swine Anti Rabbit Ig, Dako AS, diluted 1/500 in PBS-1% BSA, for 1 h, and after washing determination of OD 620 nm after incubation with 100 μL 3,3',5,5'-tetra methyl benzidine (TMB) substrate (Elisa Technologies, Lexington, Ky., US).

The reactivity of selected S100 MAb:s in immunometric assay format are shown in FIG. 1. These results show that:

S35 MAb of Group A (see Example 2.4) recognises an epitope accessible only in S100αβ, but not in S100αα and S100ββ.

S21 MAb of Group B recognises an epitope accessible both in S100ββ and S100αβ, but not accessible in S100αα.

S23 MAb of Group C recognises an epitope equally accessible in S100ββ and S100αβ, but not accessible in S100αα.

S10 MAb of Group E recognises an epitope accessible only in S100ββ, but not accessible in S100αα or S100αβ.

2. 3. Epitope Characterisation

The structural relation between the antigenic domains of the different S100 MAb was characterised by determination of possible sandwich combinations (Example 2. 3a) and inhibition of binding of S100ββ and S100αβ (Example 2.3b).

2. 3a. Dose-response Curves for Heterologous S100 EIA

S100 EIA:s were designed with S100 MAb coated in microtiter wells as described above, and horse radish peroxidase (HRP) labeled S100 MAb. The S100 MAb:s were labeled with HRP (Type V, Sigma Chemical Co., US) according to the procedure of Nakone (Nakone and Kawaoi, J Histochem Cytochem, 22: 1084–1089, 1974).

The dose-response curves for S100ββ and S100αβ were determined as follows: 50 μL of the S100ββ or S100αβ (0–100 μg/L)+100 μL of assay buffer was incubated in duplicates in the MAb coated wells for 1 h during constant shaking. After washing 100 μL of HRP S100 MAb, 2 μg/mL, was added, and the incubation continued for 1 h. After washing and incubation with 100 μL TMB substrate OD was determined at 620 nm in an ELISA reader.

2. 3b. Inhibition of binding of S100ββ and S100αβ

Inhibition studies were made to estimate the three dimensional relationship between the epitopes of the different antibodies according to the invention. If the binding of a second antibody to the complex between a first antibody and the antigen is inhibited, the epitopes of the two antibodies are overlapping or close in three dimensional structure. If the binding of a second antibody to the complex between a first antibody and the antigen is unaffected, the epitopes of the two antibodies are separated from each other.

Inhibition of binding of S100ββ and S100αβ to the S100 MAb was tested by incubation for 30 min of 50 μL S100ββ or S100αβ, 50 μg/L, +100 μL of S100 MAb, 5 μg/mL, in microtitre plates, as control 50 μL S100 antigen +100 μL PBS-1% BSA was pre-incubated in the same way. After the pre-incubation 100 μL was transferred to another microtiter plate coated with the S100 MAb to be tested, and incubated for 1 h. After washing bound S100 antigen was detected by incubation with Rabbit Anti Human S100 and HRP SwAR.

Inhibition was calculated as percent decrease in binding of S100 antigen pre-incubated with S100 MAb compared to S100 antigen pre-incubated with PBS-1% BSA.

The inhibition was performed with all antibodies as catching and inhibiting antibody. Some of the results of inhibition of selected MAb:s are shown in FIG. 2. S35 MAb (FIG. 2A) was inhibited only by itself, S34, and S72. S21 MAb (FIG. 2B) was inhibited by itself, S5, S16, S18, S21, S49, S50, S53, S54, S55, S59, S60, S62, S67, S66, S77, and S83. S23 MAb (FIG. 2C) was inhibited by itself only, i.e. recognizing a unique epitope, not recognized by any of the other MAb:s established. S25 MAb (FIG. 2D) was inhibited by itself, S11, S25, S28, S36, S43, S44, S58, and S65. S36 MAb (FIG. 2E) was inhibited by itself, S28, S36, S43, S58, and S65. Further S36 MAb was partially inhibited by S11, S25, and S44. S10 MAb (FIG. 2F) was inhibited only by itself, S12, and S13.

2. 4 Antigenic Domains

Based on reactivity with the purified S100 iso-forms (Example 2.2), inhibition of binding of S100 (Example 2.3b), and the dose-response of different antibody combinations (Example 2.3a) the antibodies were separated into different epitope groups, Group A–E, Table 1. Antibodies belonging to the same epitope group, i.e. antibodies having overlapping epitopes, inhibited each other >75%. Antibodies belonging to different epitope groups, i.e. antibodies having epitopes separated from each other, inhibited each other <40%. Separation into different subgroups was made when the inhibition differed depending on which antibody was first reacted with the antigen and which antibody was reacted with the formed antigen-antibody complex, i.e. when partial inhibition (40–75%) occurred.

TABLE 1

Epitope groups in S100.

| | Epitope group | | | | | | | |
|---|---|---|---|---|---|---|---|---|
| | B | | | D | | | | |
| A | 1 | 2 | C | 1 | 2 | 3 | E |
| S34 | S16 | S5 | S23 | S25 | S11 | S28 | S10 |
| S35 | S21 | S18 | | | S44 | S36 | S12 |
| S72 | S50 | S49 | | | | S43 | S13 |
| | S53 | S54 | | | | S58 | |
| | S60 | S55 | | | | S65 | |
| | S62 | S59 | | | | | |
| | S67 | S66 | | | | | |
| | S77 | S83 | | | | | |

EXAMPLE 3

The specificity of the assays were confirmed by determination of dose-response curves with purified S100ββ, S100αβ and S100αα obtained from Affinity Research Ltd, UK.

The lyophilised antigens were reconstituted with distilled water to a concentration of 1 μg/L.

The purity of the antigens were tested by SDS-PAGE of reduced and non-reduced samples on 8–25% polyacryl amide gels using Pharmacia Phast system according the manufacturers instructions, and stained with Comassie Brilliant Blue. Based on the evaluation of the staining purity of the antigens were estimated as >95% pure.

3. 1 Assays for Specific Determination of S100ββ

Assays specific for S100ββ without significant reactivity with S100αβ and S100αα were designed by using antibodies of Group E in combination with antibodies of Group C or Group B1. In the preferred configuration S10 MAb was used as catching antibody and S23 MAb or S 21 MAb were used as detecting antibody.

Example 3.1
Development of EIA Specific for S100ββ

S10 MAb was biotinylated with BiotinNHRS caproate ester (Sigma Chemical Co, US) using standard procedures, and used as catching antibody.

S23 MAb or S21 MAb were conjugated with HRP, Type V (Sigma Chemical Co, US) according to a modification of the Nakone procedure.

The biotinylated S10 MAb and HRP conjugated S23 or S21 MAb were used in two-site EIA according to the following protocol.

Assay Procedure
1. Add 50 μL of S100 standards (0–100 μg/L in PBS, 60 g/L BSA, pH 7.2)+100 μL of Biotin S10 MAb, 2 μg/mL, in Assay Buffer in Streptavidin coated microtiter plates (Labsystems Oy, Helsinki, Finland).
2. Incubate for 1 h±10 min with shaking
3. Wash 3 times with 5 mM Tris buffer, 0.05% Tween 40, pH 7.75.
4. Add 100 μL HRP S23 MAb (or 100 μL HRP S21 MAb), 2 μg/mL, in Assay Buffer.
5. Incubate for 1 h±10 min with shaking.
6. Wash 6 times with 5 mM Tris buffer, 0.05% Tween 40, pH 7.75.
7. Add 100 μL TMB (ELISA Technology, US)
8. Incubate 30 min±5 min
9. Determine OD 620 nm in ELISA reader.

Figure 3:
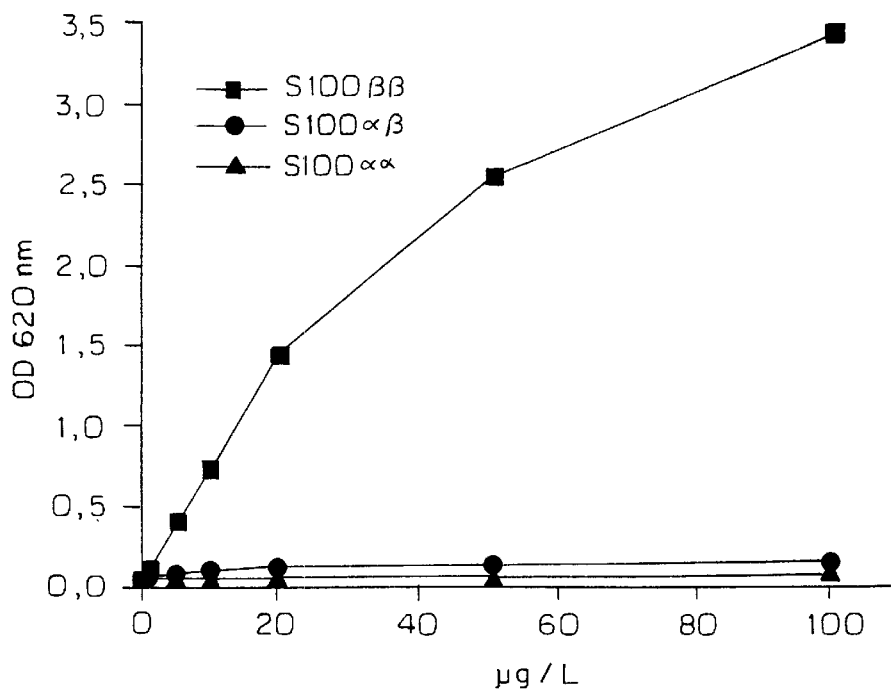
FIG. 3 shows the step of the assay that is specific for S100ββ, designed as described in Example 3.1, using Biotin S10 MAb as catching antibody and HRP S23 MAb as detecting antibody.
Figure 4:
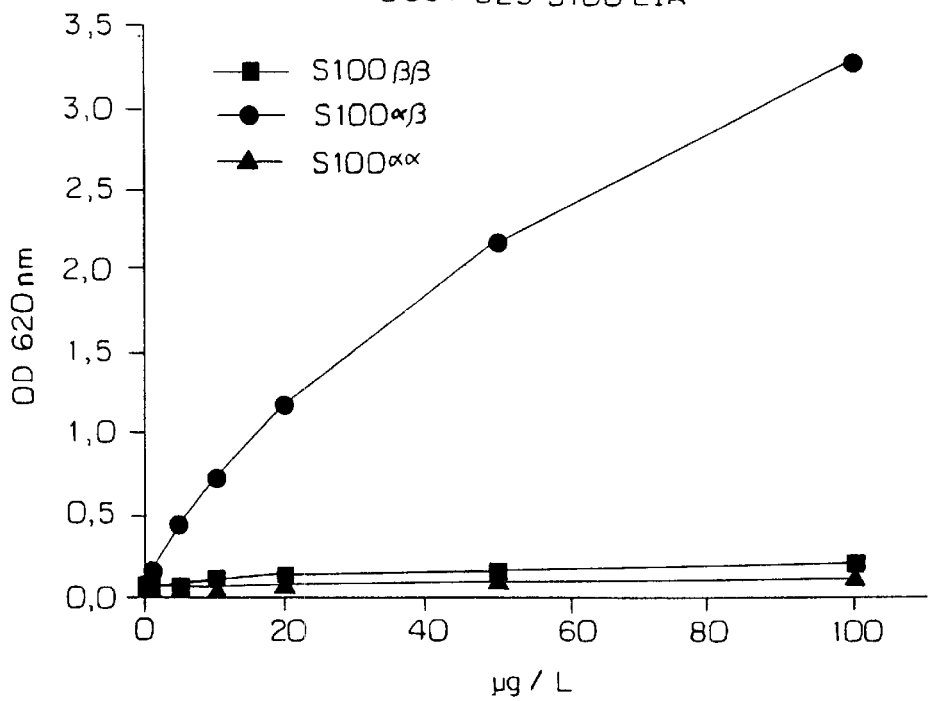
FIG. 4 shows the step of the assay that is specific for S100αβ, designed as described in Example 3.2, using Biotin S35 MAb as catching antibody and HRP S23 MAb as detecting antibody.

Dose-response curves for S100ββ, S100αβ and S100αα are shown in FIG. 3. Based on the dose-response curves the assay according to this example is specific for S100ββ, with a cross-reactivity for S100αβ and S100αα of <5% and <2%, respectively.

3.2. Assays for Specific Determination of S100αβ

Assays specific for S100αβ without significant reactivity with S100ββ and S100αα were designed by using antibodies of Group A in combination with antibodies of Group C or Group B1. In the preferred configurations S35 MAb was used as catching antibody and S23 MAb or S21 MAb were used as detecting antibody.

Example 3.2
Development of EIA Specific for S100αβ

S35 MAb was biotinylated with BiotinNHRS caproate ester (Sigma Chemical Co, US) using standard procedures, and used as catching antibody. S23 MAb or S21 MAb were conjugated with HRP (Type V, Sigma Chemcal Co., US) according to a modification of the Nakone procedure.

The biotinylated S35 MAb and HRP conjugated S23 or S21 MAb were used in two-site EIA according to the following protocol.

Assay Procedure
1. Add 50 μL of S100 standards (0–100 μg/L in PBS, 60 g/L BSA, pH 7.2) +100 μL of Biotin S35 MAb, 2 μg/mL, in Assay Buffer in Streptavidin coated microtiter plates (Labsystems Oy, Helsinki, Finland).
2. Incubate for 1 h±10 min with shaking
3. Wash 3 times with 5 mM Tris buffer, 0.05% Tween 40, pH 7.75.
4. Add 100 μL HRP S23 MAb (or 100 μL HRP S21 MAb), 2 μg/mL, in Assay Buffer.
5. Incubate for 1 h±10 min with shaking.
6. Wash 6 times with 5 mM Tris buffer, 0.05% Tween 40, pH 7.75.
7. Add 100 μL TMB, ELISA Technology, US.
8. Incubate 30 min±5 min
9. Determine OD 620 nm in ELISA reader.

Dose-response curves for S100ββ, S100αβ and S100αα are shown in FIG. 5. Based on the antibodies according to 3.3 immunoassays specific for S100αβ, with <10% and <2% cross-reactivity for S100ββ and S100αα, respectively, may be designed.

The results of the assays of Examples 3.1 and 3.2 are summerized to give total S100 i.e. the sum of S100αβ and S100ββ.

REFERENCES

Buer J, Probst M, Franzke A, Duensing A, Duensing S, Haindl J, Volkenandt M, Wittke F, Hoffman R, Ganser A, Atzpodien J. 1997. Br J Cancer 75: 1373–1376.

Henze G, Dummer R, Joller Jemelka H, Böni R, Burg G. 1997. Dermatology 194: 208–212.

Ingebrigtsen T., Romner B, Kongstad P., Langbakk B., 1995. J Neurol. Neurosurg. Psych. 59: 103–104.

Isobe T, Okuyama T., 1978. Eur J Biochem. 89: 379–388.

Isobe T., Okuyama T. 1981. Eur J. Biochem. 116: 79–86.

Isobe T, Takahashi K, Okuyama T. 184. J Neurochem. 43: 1494–1496.

Kato K., Kimura S. 1985. Biochim. Biophys. Acta 842: 146–150.

Lindholm L., Holmgren J, Svennerholm L, Fredman P, Nilsson O, Persson B, Myrvold H, Lagergård T. 1983. Int Arch Allergy and Appl. Immunol. 71: 178–181.

Michetti F., Massaro A, Russo G., Rigon O. 1980. J Neurol 44: 731–743.

Moore B W. 1965. Biochem Biophys. Res. Comm. 19: 739–744.

Moore B W. 1982. Scand J Immunol 9: 53–74.

Nakane P K, Kawaoi A. 1974. J Histochem. Cytochem., 22 1084–1090.

Persson L., Hårdemark H-G., Gustafsson J., Rundström G., Mendel-Hartvig I., Esscher T., Påhlman S. 1987. Stroke 18: 911–918.

Westaby S, Johnson P, Parry A J, Blomquist S, Solem J O, Alling A, Pillai R., Taggart D P, Grebenik C, Ståhl E. 1996. Ann Thorac Surg 61: 88–92.

Zimmer D B, Cornwall E H, Landar A and Song W. 1995. Brain Res. Bull 37: 417–429.

What is claimed is:

1. A method of quantitatively determining the total amount of S100αβ and S100ββ in a sample, which comprises:

a) contacting a first aliquot of the sample with a monoclonal antibody, or antigen binding fragment thereof, which recognizes an epitope of S100 that is accessible in S100ββ, but that is only accessible to an extent of less than 5% in S100αα and S100αβ, under conditions permitting the antibody to bind to S100ββ and form a first complex therewith;

b) determining the amount of antigen bound to said antibody, thereby determining the amount of S100ββ in the sample;

c) contacting a second aliquot of the sample with a monoclonal antibody, or antigen binding fragment thereof, which recognizes an epitope of S100 that is accessible in S100αβ, but that is only accessible to an extent of less than 5% in S100αα and S100ββ, under conditions permitting the antibody to bind to S100αβ and form a second complex therewith; and d) determining the amount of antigen bound to said antibody, thereby determining the amount of S100αβ in the sample.

2. A kit for assaying the amount of S100ββ comprising a monoclonal antibody, or antigen binding fragment thereof, which recognises an epitope of S100 that is accessible in S100ββ, but that is only accessible to an extent of less than 5% in S100αα and S100αβ.

3. A kit according to claim 2, wherein the monoclonal antibody is a catching antibody and the kit further comprises a detecting antibody.

4. A kit according to claim 3, wherein the detecting antibody is an antibody, or antigen binding fragment thereof, which is produced by hybridoma cell line S23:2 given ECACC Accession No. 98082617.

5. A kit according to claim 2, wherein the monoclonal antibody is an antibody produced by the hybridoma cell line S10:3 given ECACC Accession No. 98082619.

6. A kit according to claim 5, wherein the monoclonal antibody is a catching antibody and the kit further comprises a detecting antibody.

7. A kit according to claim 6, wherein the detecting antibody is an antibody, or antigen binding fragment thereof, which is produced by hybridoma cell line S23:2 given ECACC Accession No. 98082617.

8. A kit for assaying the amount of S100αβ comprising a monoclonal antibody, or antigen binding fragment thereof, which recognises an epitope of S100 that is accessible in S100αβ, but that is only accessible to an extent of less than 5% in S100αα and S100ββ.

9. A kit according to claim 8, wherein the monoclonal antibody is a catching antibody and the kit further comprises a detecting antibody.

10. A kit according to claim 9, wherein the detecting antibody is an antibody, or antigen binding fragment thereof, which is produced by hybridoma cell line S23:2 given ECACC Accession No. 98082617.

11. A kit according to claim 8, wherein the monoclonal antibody is an antibody produced by the hybridoma cell line S35:2 given ECACC Accession No. 98082616.

12. A kit according to claim 11, wherein the monoclonal antibody is a catching antibody and the kit further comprises a detecting antibody.

13. A kit according to claim 12, wherein the detecting antibody is an antibody, or antigen binding fragment thereof, which is produced by hybridoma cell line S23:2 given ECACC Accession No. 98082617.

14. The hybridoma cell line S10:3 given ECACC Accession No. 98082619.

15. The hybridoma cell line S35:2 given ECACC Accession No. 98082616.

16. The hybridoma cell line S23:2 given ECACC Accession No. 98082617.

17. A method of quantitatively determining the total amount S100ββ in a sample, comprising
  a) contacting an aliquot of the sample with a monoclonal antibody, or antigen binding fragment thereof, which recognizes an epitope of S100 that is accessible in S100ββ, but that is only accessible to an extent of less than 5% in S100αα and S100αβ, under conditions permitting the antibody to bind to S100ββ and form a complex therewith; and
  b) determining the amount of antigen bound to said antibody, thereby determining the amount of S100ββ in the sample.

18. A method of quantitatively determining the total amount of S100αβ in a sample, comprising:
  a) contacting an aliquot of the sample with a monoclonal antibody, or antigen binding fragment thereof, which recognizes an epitope of S100 that is accessible in S100αβ, but that is only accessible to an extent of less than 5% in S100αα and S100ββ, under conditions permitting the antibody to bind to S100αβ and form a complex therewith; and
  b) determining the amount of antigen bound to said antibody, thereby determining the amount of S100αβ in the sample.

* * * * *